(12) United States Patent  
Ichizawa

(10) Patent No.: US 8,488,744 B2  
(45) Date of Patent: Jul. 16, 2013

(54) X-RAY MEASUREMENT APPARATUS

(75) Inventor: Yasushi Ichizawa, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 206 days.

(21) Appl. No.: 12/954,710

(22) Filed: Nov. 26, 2010

(65) Prior Publication Data

US 2011/0122993 A1    May 26, 2011

(30) Foreign Application Priority Data

Nov. 26, 2009    (JP) .................... 2009-268585

(51) Int. Cl.  
G21K 3/00    (2006.01)

(52) U.S. Cl.  
USPC ............... 378/156; 378/158; 378/204

(58) Field of Classification Search  
USPC ............... 378/147, 149, 150, 154, 156–159, 378/203, 204  
See application file for complete search history.

(56) References Cited

U.S. PATENT DOCUMENTS

| | | | |
|---|---|---|---|
| 3,944,833 A | 3/1976 | Hounsfield | |
| 4,286,167 A | 8/1981 | La Riviere | |
| 5,293,417 A | 3/1994 | Wei et al. | |
| 5,442,675 A * | 8/1995 | Swerdloff et al. | 378/65 |
| 2007/0104320 A1 | 5/2007 | Arenson et al. | |

FOREIGN PATENT DOCUMENTS

| | | |
|---|---|---|
| EP | 1498908 A2 | 7/2004 |
| JP | 55160900 | 12/1980 |
| JP | 58-209273 A | 12/1983 |
| JP | 60-143000 A | 7/1985 |
| JP | 61-35304 A | 2/1986 |
| JP | 2000-245731 A | 9/2000 |
| JP | 2000-321359 A | 11/2000 |
| JP | 2003-57397 A | 2/2003 |
| JP | 2003-517577 T | 5/2003 |
| JP | 2006-288554 A | 10/2006 |
| WO | WO 2005091225 A1 | 9/2005 |
| WO | WO 2008068690 A2 | 6/2008 |

OTHER PUBLICATIONS

Japanese Office Action issued on Oct. 25, 2011 in corresponding Japanese Application No. 2009-268585.  
Communication dated Nov. 22, 2011 from the European Patent Office in counterpart European application No. 10192649.1.  
Japanese Office Action dated Oct. 25, 2011 issued in corresponding Japanese Patent Application No. 2009-268585.

* cited by examiner

*Primary Examiner* — Jurie Yun  
(74) *Attorney, Agent, or Firm* — Sughrue Mion, PLLC

(57) ABSTRACT

An X-ray measurement apparatus includes an X-ray source configured to emit an X-ray to irradiate a specimen with the X-ray, a collimator configured to shape a beam of the X-ray emitted from the X-ray source into a sliced fan-shaped beam x-ray, a flux shield configured to block a part of a flux of the fan-shaped beam X-ray so as to suppress beam hardening while adjusting an energy intensity distribution of the flux, the flux shield being placed between the collimator and the specimen, and an X-ray detector configured to detect a dose transmitted through the specimen.

16 Claims, 7 Drawing Sheets

LAMINATED LAYERS WITH SLIT
PITCHES SHIFTED FROM ONE
LAYER FROM ANOTHER

X-RAY MEASUREMENT APPARATUS

This application claims priority from Japanese Patent Application No. 2009-268585, filed on Nov. 26, 2009, the entire contents of which are herein incorporated by reference.

TECHNICAL FIELD

The present disclosure relates to an X-ray measurement apparatus which irradiates a specimen with an X-ray emitted from an X-ray source and detects a dose transmitted through the specimen by an X-ray detector. The present disclosure provides an X-ray measurement apparatus in which a shield for adjusting a spatial intensity distribution of a flux (radiant flux) from the X-ray source is improved to suppress the intensity of the flux in a central portion while reducing occurrence of beam hardening. The beam hardening is technically disclosed in Patent Document 1.

RELATED ART

FIG. 6 is a perspective view showing a configuration example of an apparatus for measuring a basis weight of a specimen (such as paper, a film, a thin film sheet, etc.). A conical beam X-ray B1 from an X-ray source 1 is passed through a collimator 2 having a slit 21 so as to be shaped into a sliced fan-shaped beam X-ray B2. A specimen 3 running in the direction of an arrow F is irradiated with the fan-shaped beam X-ray B2.

The transmitted dose of the X-ray transmitted through the specimen 3 is measured by a line sensor of an X-ray detector 4 which is disposed under the specimen so as to face the X-ray source 1. A specimen whose basis weight is known is measured in advance, and a standard curve L is drawn as shown in FIG. 7. A basis weight measurement of a specimen is performed based on the relationship between transmitted dose and basis weight. A coating amount measurement or a film thickness measurement of a specimen can be performed by the similar method.

As the X-ray detector 4, a combination of a scintillator and a semiconductor photo acceptance device (CCD, C-MOS, etc.) may be used. The combination of the scintillator and the semiconductor photo acceptance device measures the radiation dose in such a manner that the scintillator is phosphorated when receiving an electron beam or photon energy (electromagnetic wave), and the phosphorescent intensity is converted into charges by the semiconductor photo acceptance device which is sensitive to visible light. Alternatively, a direct conversion type radiation detection device or the like may be used as the X-ray detector 4. In the direct conversion type radiation detection device, an electron beam or photon energy (electromagnetic wave) is received directly by a semiconductor photo acceptance device and converted into an amount of charges corresponding to the radiation intensity.

The output of the transmitted dose detected by the X-ray detector 4 is typically of about 10 to 12 bits (1024 to 4096 gradations). The output varies depending on the distance between the X-ray source 1 and the X-ray detector 4 or the value of the X-ray source radiation angle (20 shown in FIG. 6). FIG. 8 shows an example of characteristic of the output of the X-ray detector 4.

The central portion of the X-ray detector 4 having a linear shape is near to the X-ray source 1. The sensitivity to the transmitted dose in the periphery of the X-ray detector 4 is lowered in accordance with a so-called cosine fourth law with respect to a radiation angle θ. Therefore, measurement conditions such as the output of the X-ray source 1, the exposure time (integrated time), etc. are decided in order not to provide saturation for the maximum output in the central portion.

The measurement accuracy in the central portion which is high in dose differs from that in the periphery (outermost portion) which is low in dose. Decrease of about ½ is not a problem particularly. However, if the distance between the X-ray source 1 and the X-ray detector 4 is short or if the intensity of the radiation angle of the X-ray source 1 has excessive directivity, only a fraction of the output in the central portion can be obtained in the periphery (outermost portion). Thus, desired measurement accuracy cannot be obtained in the periphery (outermost portion).

Therefore, as shown in FIG. 9, a flux shield 5 which is formed stepwise to be thicker in the central portion is inserted in any arbitrary position between the X-ray source 1 and the specimen 3 so as to limit the transmitted dose only in the central portion which is high in flux.

The material of the flux shield 5 is generally a metal foil sheet or a thin plate of aluminum, copper, iron, stainless steel or the like, a resin material such as a PET or acrylic plate, a composite material having a resin base material deposited with metal, or the like.

Although the flux shield 5 shown in FIG. 9 is shaped into three steps, it is not necessary to be always three steps. The flux shield 5 may be shaped by processing such as molding or cutting so that the thickness thereof can vary continuously. Alternatively, the flux shield 5 does not have to have an integrated shape but may have a structure in which a larger number of thin sheets are laminated in the central portion. In such a manner, the shield effect can be adjusted easily while spatially continuous attenuation can be obtained.

FIG. 10 shows the output characteristic of the X-ray detector 4 in the case where the dose in the central portion is limited in this manner. When the three-stepped flux shield 5 is inserted, four differences in step appear totally in the output characteristic, but decrease in the periphery can be suppressed as compared with that in the central portion.

When the number of steps of the flux shield 5 is increased or when the steps of the flux shield 5 are made continuous to each other, each of the differences in step in the output characteristic can be made less. The dose is indeed decreased. However, as long as the dose in the central portion and the dose in the periphery can be uniform, satisfactory accuracy in the periphery can be secured when the exposure time is elongated or the output of the X-ray source 1 is increased.

In addition, the dose in the central portion may be limited more aggressively because slight reduction in the flux intensity in the central portion leads to a uniform dose after transmission.

Patent Document 1 JP-T-2003-517577

FIG. 11 shows an X-ray intensity distribution immediately before an X-ray reaches the specimen 3 when the dose in the central portion is limited by the flux shield 5 having the related-art configuration. Photon energy is radiated with a continuous spectrum corresponding to an X-ray tube voltage. However, the photon energy contributing to measurement has an energy distribution A in the outermost portion of the specimen due to absorption in a low energy band (area D in FIG. 11) not higher than several keV by atmospheric absorption and a radiation window material (thin film of beryllium, mica, or the like).

Even when a flux radiated from the same X-ray source is limited only in the central portion by the flux shield, the attenuation of a short-wavelength and high-energy X-ray is low as shown by the reference sign B in FIG. 11. The energy distribution at the center of the specimen is shown by the reference sign C in FIG. 11. As illustrated, short-wavelength beam hardening occurs more intensively in the central portion than in the periphery (outermost portion).

Such a phenomenon occurs because the attenuation of the low-energy X-ray shown by the reference sign B is increased but the high-energy X-ray is not attenuated as the shield effect is stronger. As a result, there occurs a so-called beam hardening phenomenon in which peak energy is shifted to the high-energy side in the central portion of the specimen.

When a thin-film specimen is measured with a high-energy X-ray, a satisfactory attenuation characteristic of the specimen cannot be obtained. Thus, a measurement result cannot be obtained with a high measurement accuracy. In addition, the photon energy flux which measures the transmission characteristic differs between the central portion and the periphery. Accordingly, the measurement result does not coincide with the standard curve (relationship between attenuation characteristic and basis weight) obtained in advance as shown in FIG. 7. That is, when a specimen with the same thickness (basis weight) as a specimen measured in advance is measured, the reduced output in the periphery leads to wrong measurement as if the specimen were thick.

SUMMARY

Exemplary embodiments of the present invention provide an X-ray measurement apparatus in which a spatial intensity distribution of a flux is improved while suppressing occurrence of beam hardening, and the energy distribution and the dose of the flux are uniform between a central portion and a periphery so that an error in measurement caused by a measurement position can be reduced.

An X-ray measurement apparatus, according to an exemplary embodiment, comprises:

an X-ray source configured to emit an X-ray to irradiate a specimen with the X-ray;

a collimator configured to shape a beam of the X-ray emitted from the X-ray source into a sliced fan-shaped beam x-ray;

a flux shield configured to block a part of a flux of the fan-shaped beam X-ray so as to suppress beam hardening while adjusting an energy intensity distribution of the flux, the flux shield being placed between the collimator and the specimen; and an X-ray detector configured to detect a dose transmitted through the specimen.

Other features and advantages may be apparent from the following detailed description, the accompanying drawings and the claims.

DETAILED DESCRIPTION

Figure 1:
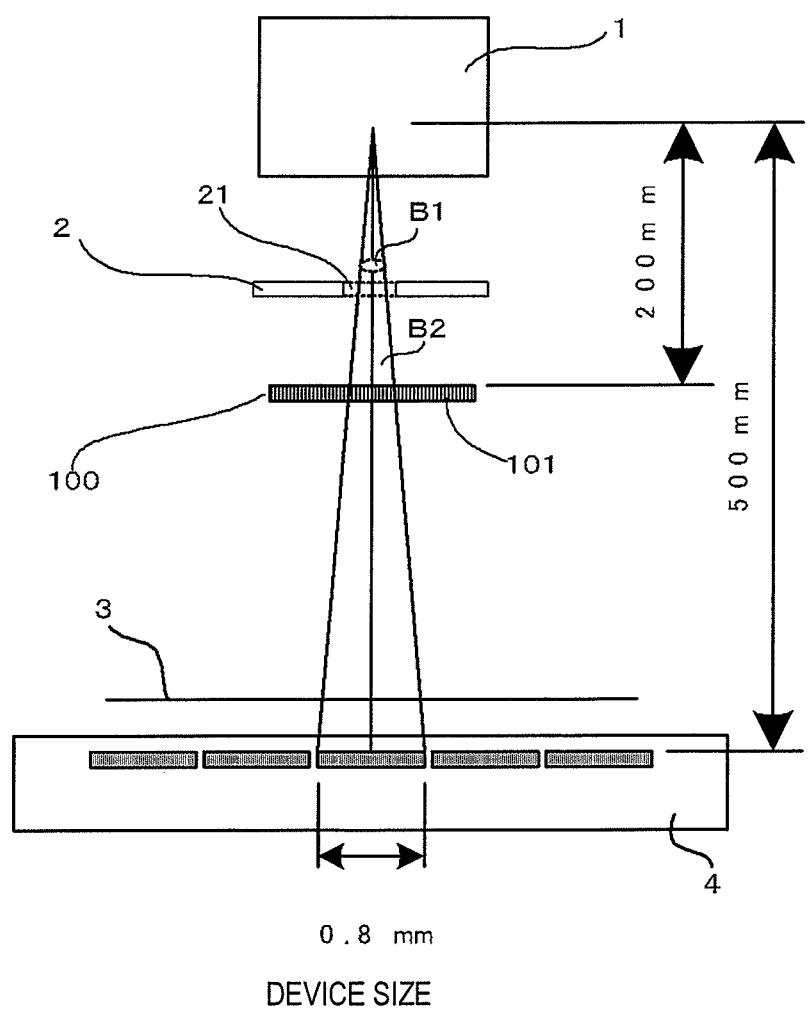
FIG. 1 is a sectional view showing an X-ray measurement apparatus according to an embodiment of the invention.
Figure 6:
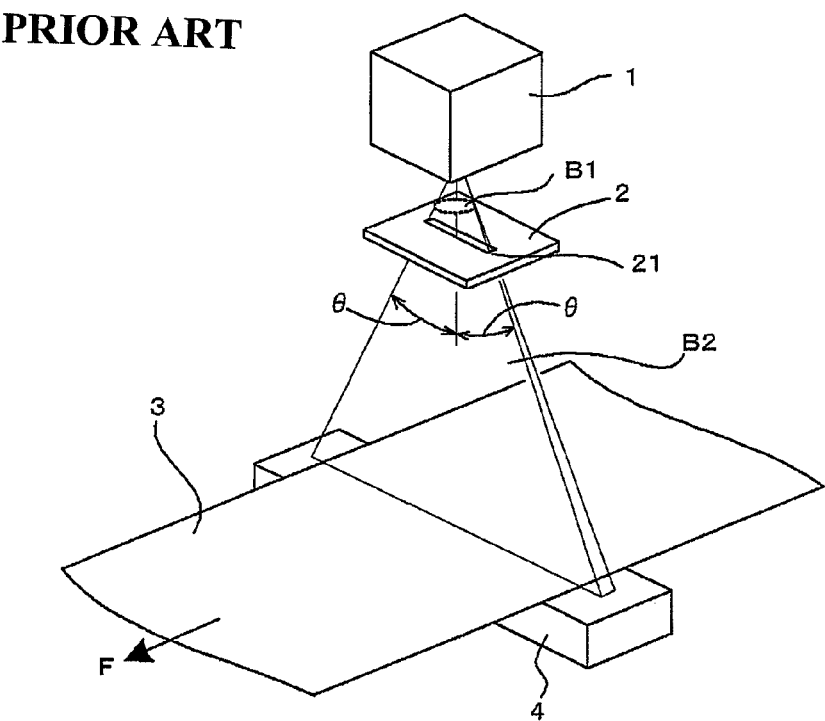
FIG. 6 is a perspective view showing a configuration example of an apparatus for measuring a basis weight of a specimen.
Figure 7:
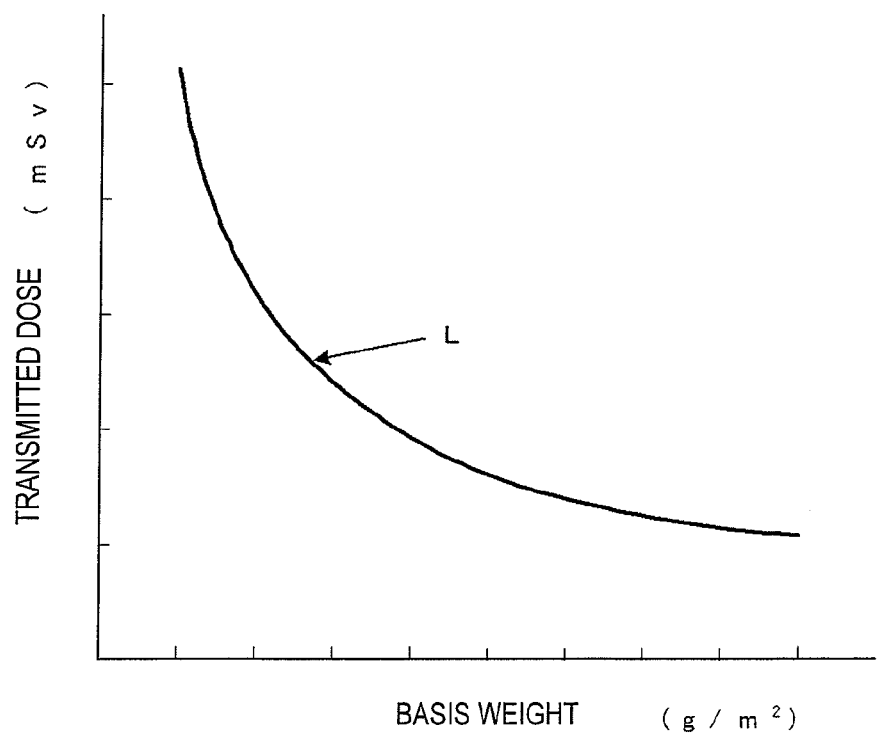
FIG. 7 is a view showing a relationship between a basis weight and a transmitted dose.
Figure 8:
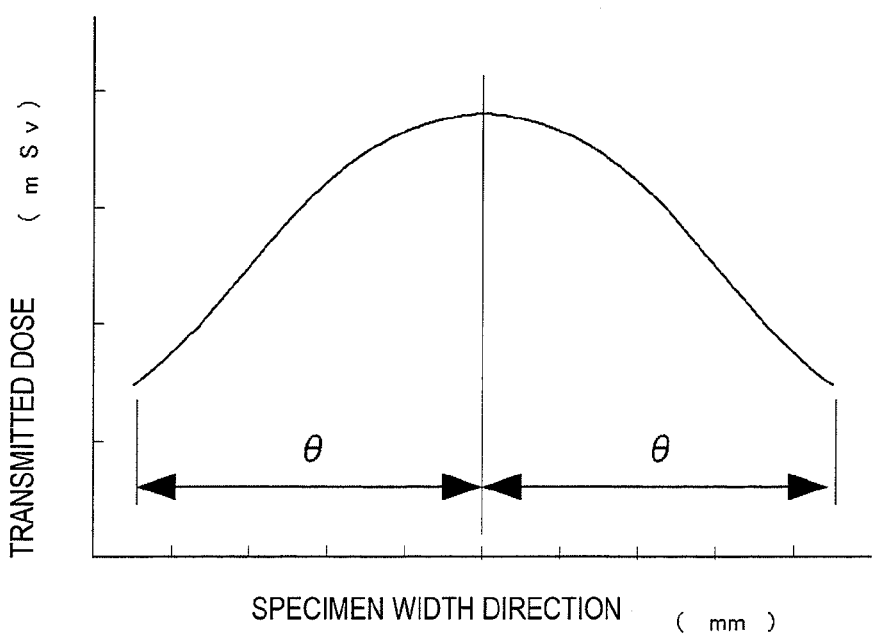
FIG. 8 is a view showing a relationship between specimen width direction and a transmitted dose.
Figure 9:
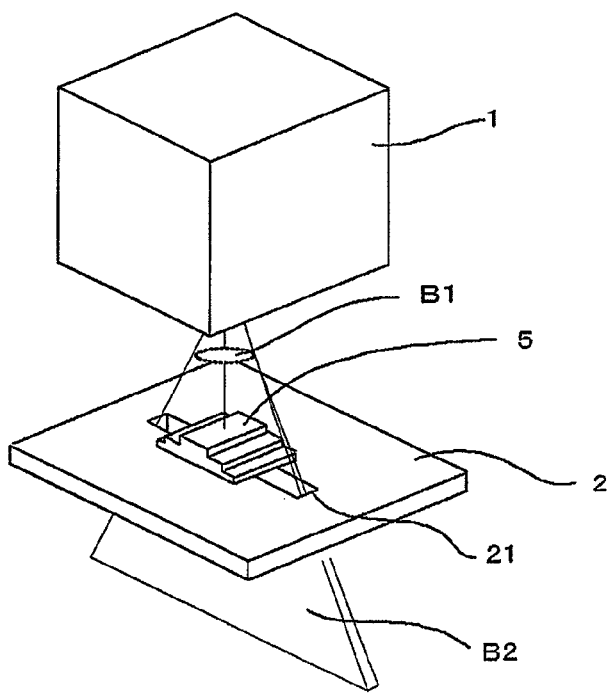
FIG. 9 is a perspective view showing a configuration example of a basis weight measuring apparatus of a specimen having a flux shield.
Figure 10:
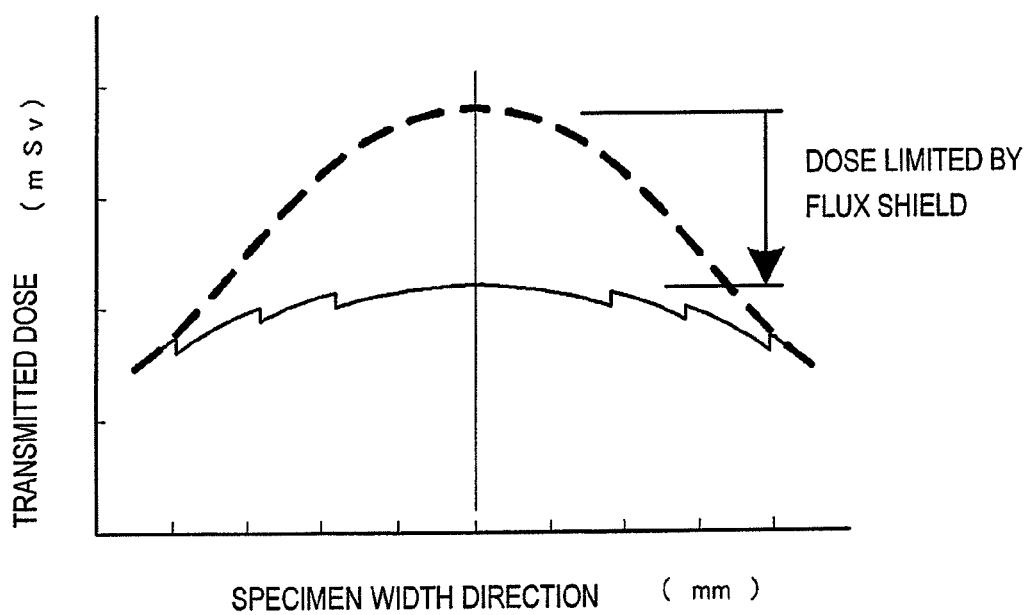
FIG. 10 is a view showing a relationship between specimen width direction and a transmitted dose when the flux shield is used.
Figure 11:
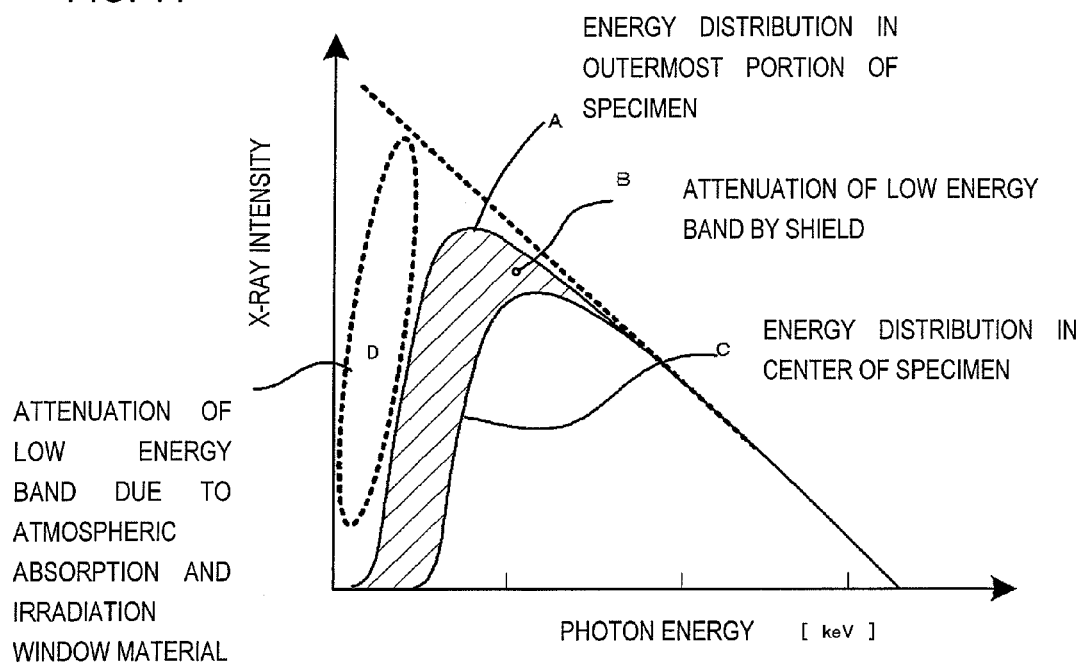
FIG. 11 is a view showing a relationship between photon energy and X-ray intensity for explaining beam hardening by the flux shield.

Exemplary embodiments will be described below in detail with reference to the drawings. FIG. 1 is a sectional view showing an X-ray measurement apparatus according to an embodiment of the invention. Elements the same as those in the related-art configuration described with reference to FIG. 6 are referred to by the same numerals respectively, and description thereof will be omitted.

The embodiment is characterized by a configuration in which a flux shield 100 for partially passing or blocking a flux of a fan-shaped beam X-ray B2 shaped by a collimator 2 is inserted and disposed between an X-ray source 1 and a specimen 3 and behind the collimator 2.

The flux shield 100 may be inserted near the rear of the collimator 2 or inserted just before the specimen 3 and at a distance from the collimator 2. The fundamental configuration of a measurement system is the same as the related-art configuration of FIG. 6.

Figure 2:
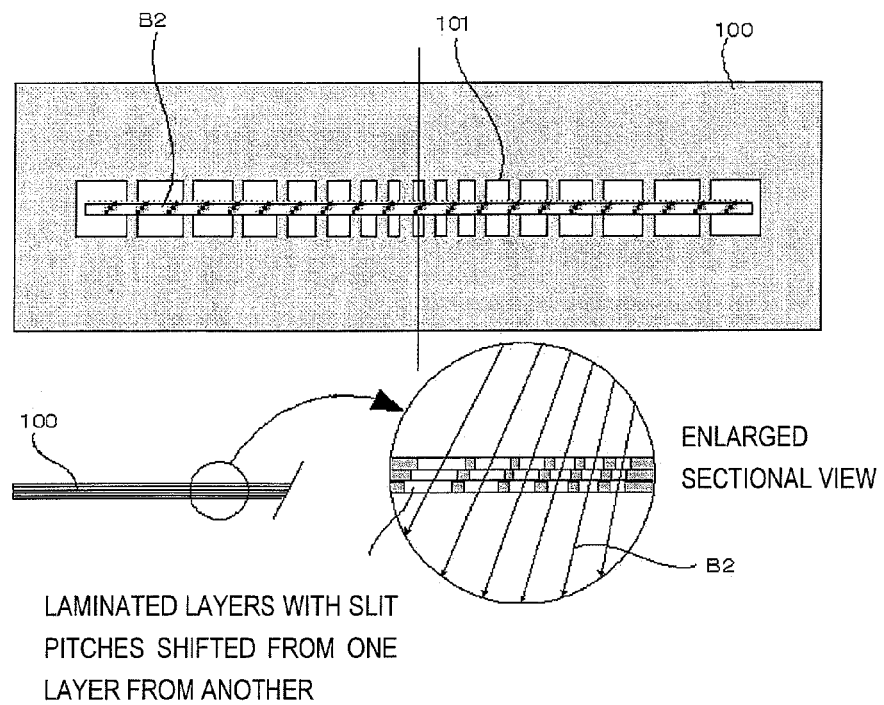
FIG. 2 is a plan view showing a configuration example of a flux shield used in the embodiment of the invention.

FIG. 2 is a plan view showing a configuration example of the flux shield 100 used in the embodiment of the invention. The flux shield 100 has a plurality of fine slits 101 for passing or blocking the fan-shaped beam X-ray B2. The slit width increases in a direction from the central portion toward the peripheral portion so that the fan-shaped beam X-ray B2 blocking rate is high in the central portion while the fan-shaped beam X-ray B2 blocking rate decreases stepwise toward the peripheral portion.

In the illustrated structure, fine holes (slits) are formed by etching in a shield material (copper, stainless steel, iron, brass, tungsten, lead, or an alloy of those materials), which is comparatively thin in a range of from about several tens to several hundreds of micrometers. When radiation rays cannot be absorbed satisfactorily by a single shield sheet, a plurality of shield sheets are laminated in tight contact with each other. As illustrated in the expanded view of FIG. 2, it is preferable to change the pitch of slits from one sheet to another in accordance with the inclination of the flux.

The size of each slit 101 must be sufficiently small relative to the size of each radiation detection device of the X-ray detector 4. If the slits 101 are large in terms of size, uniform measurement cannot be performed among radiation detection devices, but ripples unique to each device occur due to the shield structure so that correct measurement cannot be achieved.

Figure 3:
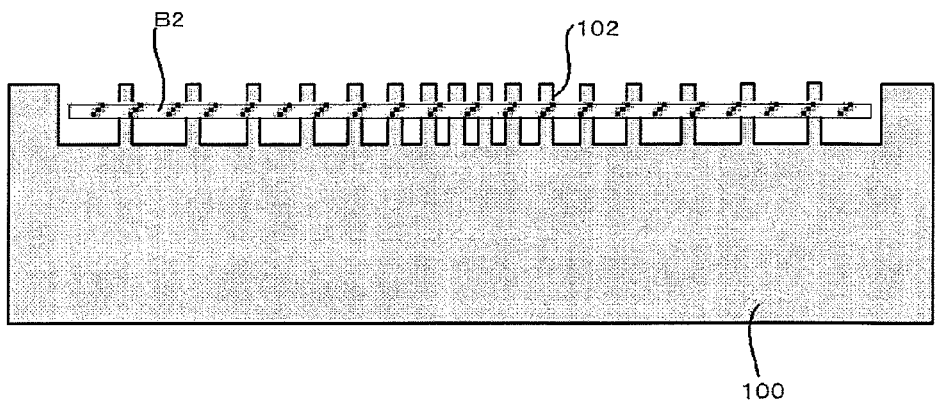
FIG. 3 is a plan view showing another configuration example of the flux shield used in the embodiment of the invention.

FIG. 3 is a plan view showing another configuration example of a flux shield used in the embodiment of the invention. The configuration is characterized not by the slits formed by etching in FIG. 2 but by opening portions 102 (grooves) formed by grooving. The configuration has the same operation and effect as those in FIG. 2 but processing is easy.

The size of the slits 101 will be considered in the configuration shown in FIG. 1. Assume that a size of each detection device is 0.8 mm by 0.8 mm. When the distance between the focus position of the X-ray source 1 and the X-ray detector 4 is 500 mm and the distance between the focus position of the X-ray source 1 and the fine slit type flux shield 100 is 200 mm, the size equivalent to one device is expressed as $0.8 \times (200/500) = 0.32$ mm when the X-ray passes through the flux shield 100.

When each slit is sufficiently small relative to the size equivalent to one device, it is possible to prevent ripples due to the fine slit type flux shield 100 from occurring. For example, the sufficiently small slit can be explained as follows. That is, for 50% shield with slits about 0.03 mm wide, the slits about 0.03 mm wide may be provided continuously at a pitch of 0.06 mm.

With such a design, a flux transmitted through five slits reaches one device. To lower the transmissivity in the central portion to 50% and permit transmissivity of 100% in the periphery which is the lowest in dose, the slit width is expanded to change the area ratio between ribs and slits (opening portions) so that the transmitted dose can be controlled desirably.

Figure 4:
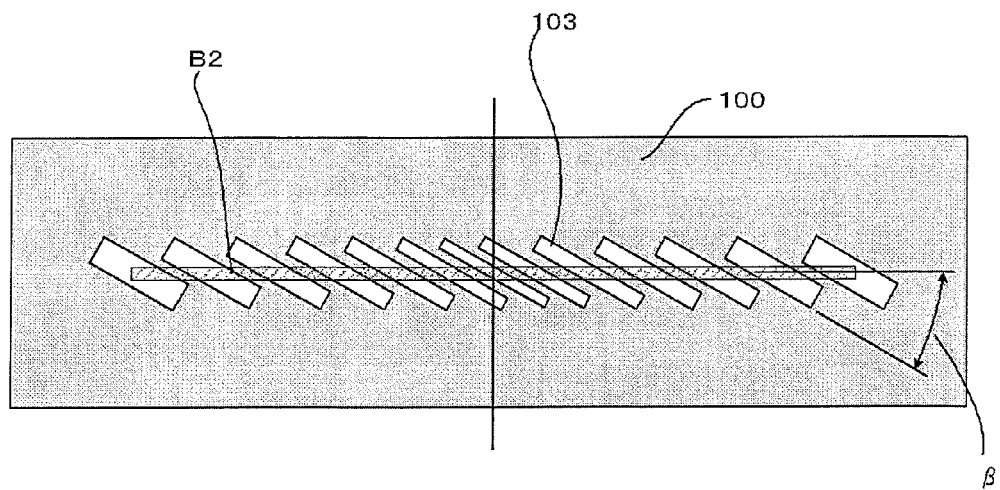
FIG. 4 is a plan view showing a further configuration example of the flux shield used in the embodiment of the invention.

FIG. 4 is a plan view showing a further configuration example of the flux shield 100 used in the embodiment of the invention. Although the longitudinal direction of each slit 101 shown in FIG. 2 is perpendicular to the fan-shaped beam X-ray B2, the longitudinal direction of each slit 103 in the configuration of FIG. 4 has an inclination $\beta$ to the fan-shaped beam X-ray B2.

When the fine opening portions are inclined at a predetermined angle in this manner, there is an effect that fluctuation in each detection device can hardly occur in comparison with the case where the opening portions are provided to be perpendicular. It is therefore possible to roughen the degree of fine processing to some extent. Further, the flux shield 100 can be used closely to the X-ray source 1. Thus, the flux shield can be miniaturized and structurally integrated with the X-ray source easily.

Figure 5:
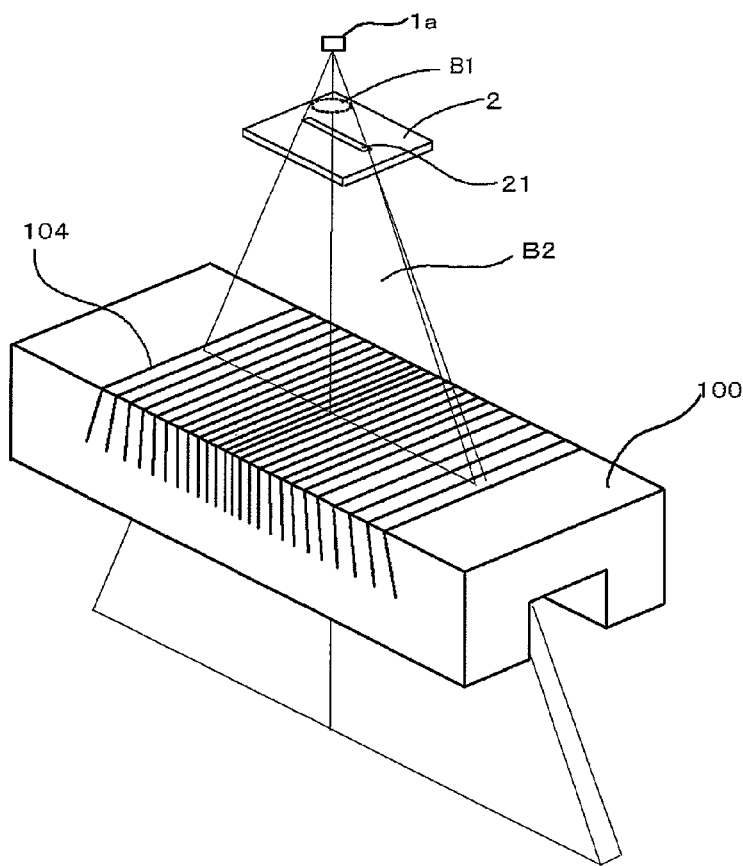
FIG. 5 is a perspective view showing a further configuration example of the flux shield used in the embodiment of the invention.

FIG. 5 is a perspective view showing a further configuration example of the flux shield used in the embodiment of the invention. This configuration example is characterized in that grooves are formed not by etching shown in FIGS. 2 to 4 but by a processing method based on electric discharge machining (wire cut) using a wire cut processing machine.

According to this processing method, one single sheet of a comparatively thick plate material (about several millimeters) which has a shield effect by itself is grooved like comb teeth by a small-diameter wire to form grooves each having a width of several tens of micrometers. In the same manner as in FIGS. 2 to 4, grooves are formed densely in a portion where the transmissivity should be lowered while grooves are formed sparsely in a portion where the transmissivity should be increased. Further, the comb teeth are formed to be divergent like a fan shape in accordance with the angle of irradiation from the focus of the X-ray source 1. In this embodiment, the single sheet of the comparatively thick plate material is used; however, a single sheet of a plate material whose material has a shield effect by itself may be used.

Although the slits or grooves in FIGS. 2 to 5 are explained one-dimensionally, the slits or grooves (opening portions) may be developed two-dimensionally and formed into spiral slits or grooves (opening portions). Further, ribbon-like foil may be vorticosely wound (through spacers etc.) densely in the central portion and sparsely in the periphery.

When the flux shield 100 used in the embodiment is combined with the function of the X-ray detector (line sensor) 4 in which gain and offset can be set for each radiation detection device, measurement can be performed with a higher accuracy.

The flux shield 100 used in the embodiment can be also effectively used as a shield unit for making the irradiation dose to a β-ray detector uniform in a measurement apparatus using a β-ray as a radiation source.

According to the embodiment of the invention, the following effects can be expected.

(1) A dose in a central portion which is high in dose is limited so that the dose can be uniform between the periphery and the central portion. Thus, the output of the X-ray detector can be uniform to solve a problem that a satisfactory dynamic range cannot be secured in some measurement site.

(2) Beam hardening can be suppressed while the dose in the central portion which is high in dose is limited. Thus, a standard curve obtained in a representative portion such as the central portion coincides with any portion of the measurement range with a high accuracy.

(3) Since a uniform dose can be applied, a good sensitive dose can be selected for a specimen even if the specimen is very thin. Accordingly, the effect of improvement is great particularly under the conditions of irradiation from a short distance at which the dose distribution becomes intensive.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An X-ray measurement apparatus comprising:
an X-ray source configured to emit an X-ray to irradiate a specimen with the X-ray;
a collimator configured to shape a conical beam of the X-ray emitted from the X-ray source into a sliced fan-shaped beam x-ray;
a flux shield placed between the collimator and the specimen and configured to pass or block a part of a flux of the fan-shaped beam X-ray so as to suppress beam hardening while adjusting an energy intensity distribution of the flux; and
an X-ray detector configured to detect a dose transmitted through the specimen;
wherein the flux shield is substantially plate shaped, having a substantially planar major surface with a central portion and a peripheral portion, said flux shield having formed therein a plurality of slits, a plurality of holes, or a plurality of opening portions,
wherein, the plurality of slits, the plurality of holes, or the plurality of opening portions are arranged varyingly in said central portion and peripheral portion so as to effect said passing or blocking of the fan-shaped X-ray,
wherein, said plurality of slits, the plurality of holes, or the plurality of opening portions are formed by fine processing, and
wherein, said plurality of slits, the plurality of holes, or the plurality of opening portions are sized to be small relative to a size and a pitch of a detection device of the X-ray detector.

2. The X-ray measurement apparatus according to claim 1, wherein the flux shield is formed to increase a shield rate of the flux to be transmitted through a central portion of the flux shield where the flux has a largest dose based on a dose distribution or an energy intensity distribution of the flux.

3. The X-ray measurement apparatus according to claim 1, wherein the flux shield is formed to have a dose distribution or an energy intensity distribution of the flux uniform between a central portion and a peripheral portion of the distribution.

4. The X-ray measurement apparatus according to claim 1, wherein the slits, the holes, or the opening portions of the flux shield are arranged in irregular intervals, and
wherein a dose distribution and an energy intensity distribution of the flux are controlled by an area ratio between the slits or holes or opening portions and ribs.

5. The X-ray measurement apparatus according to claim 1, wherein the flux shield includes a plurality of laminated metal foil sheets or metal thin plates, and each of the metal foil sheets or metal thin plates has the plurality of slits, the plurality of holes, or the plurality of opening portions.

6. The X-ray measurement apparatus according to claim 5, wherein pitches of the slits, the holes, or opening portions of the respective metal foil sheets or metal thin plates are different from each other based on a divergence from a focus point of the X-ray source.

7. The X-ray measurement apparatus according to claim 5, wherein a pitch of said slits, holes or opening portions is changed from one sheet to another in accordance with an inclination of the flux of the fan-shaped beam.

8. The X-ray measurement apparatus according to claim 1, wherein the flux shield is composed of a single sheet of a plate material whose material or thickness has a flux shield effect, and the flux shield has said opening portions defined by a comb teeth shape structure which is formed by fine processing.

9. The X-ray measurement apparatus according to claim 8, wherein the comb teeth shape structure is formed to be a divergent fan shape based on a divergence from a focus point of the X-ray source.

10. The X-ray measurement apparatus according to claim 9, wherein grooves are formed densely in a portion where the transmissivity is to be low while grooves are formed sparsely in a portion where the transmissivity is to be high.

11. The X-ray measurement apparatus according to claim 8, wherein said single sheet is several millimeters thick.

12. The X-ray measurement apparatus according to claim 1, wherein widths of the slits, the holes, or the opening portions increase in a direction from the central portion toward the peripheral portion of the flux shield.

13. The X-ray measurement apparatus according to claim 1, wherein
a longitudinal direction of each of the slits, the holes, or the opening portions has an inclination to the fan-shaped beam X-ray.

14. The X-ray measurement apparatus according to claim 1, wherein the thickness of a material of said flux shield having said slits, holes or opening portions is in a range of from several tens to several hundreds of micrometers.

15. The X-ray measurement apparatus according to claim 1, wherein said slits, holes or opening portions are formed two-dimensionally and have a spiral form.

16. The X-ray measurement apparatus according to claim 1, further comprising ribbon-like foil vorticosely wound densely in the central portion and sparsely in the peripheral portion.

* * * * *